United States Patent [19]

Ferlut

[11] Patent Number: 4,736,047

[45] Date of Patent: Apr. 5, 1988

[54] PROCESS FOR THE PREPARATION OF HEXAALKYLDISILANE

[75] Inventor: Jean-Serge Ferlut, Salindres, France

[73] Assignee: Rhone-Poulenc Chimie, France

[21] Appl. No.: 68,127

[22] Filed: Jun. 30, 1987

[30] Foreign Application Priority Data

Jul. 25, 1986 [FR] France ................... 8610990

[51] Int. Cl.⁴ .............................................. C07F 7/08
[52] U.S. Cl. ................................................... 556/430
[58] Field of Search ......................................... 556/430

[56] References Cited

U.S. PATENT DOCUMENTS 4,291,167  9/1981  Allain et al. ................. 556/430
4,309,556  1/1982  Allain et al. ................. 556/430
4,578,495  3/1986  Soula et al. ............... 556/430 X

FOREIGN PATENT DOCUMENTS 49-42616  4/1974  Japan ........................ 556/430

OTHER PUBLICATIONS

Otto Bayer Leverkusen and Eugene Muller; Methods of Organic Chemistry, (Houben-Weyl), 1980, vol. XIII/5, pp. 300–303.

Primary Examiner—Paul F. Shaver
Attorney, Agent, or Firm—Finnegan, Henderson, Farabow, Garrett & Dunner

[57] ABSTRACT

A process for the preparation of hexaalkyldisilane. A trialkylsilane halide is brought into contact with an alkali metal, a salt and a phase transfer agent.

13 Claims, No Drawings

PROCESS FOR THE PREPARATION OF HEXAALKYLDISILANE

The present invention relates to a new process for the preparation of hexaalkyldisilane. More precisely, it relates to a process for the preparation of hexaalkyldisilane from trialkylsilane halide.

The different methods known for the synthesis of hexaalkyldisilanes are of two general types. The first consists in bringing a trialkylsilane chloride into contact with a metal (lithium, potassium or sodium) in ether or tetrahydrofuran or in dipolar aprotic solvents, essentially hexamethylphosphoramide. It is described, for example, by Gilman, Shiina, Aoki, Gaj, Wittenberg and Brennan in the Journal of Organometallic Chemistry 13 (1968) 323–328 and by Sakurai and Okada in the Journal of Organometallic Chemistry 36 (1972) C 13. The hexamethyldisilane yields reported never exceed 76% despite relatively long reaction times (approximately 60 hours).

A slightly different method which employs lithium, a chloromethylsilane and ultrasonics is described, for example, by Boujouk and Han in Tetrahedron Letters, 22, 39, pp. 3813–3814, 1981. The hexaalkyldisilane yields obtained are of the order of 40%.

This first method cannot be used on an industrial scale because solvents of the ether or the hexamethylphosphoramide type and metals of the lithium type can be unsafe.

The second basic method for the synthesis of hexaalkyldisilanes is described, for example, in U.S. Pat. No. 4,309,556, and consists of reacting di(chloromethyl)disilane with a chlorinated organomagnesium compound in tetrahydrofuran. This method cannot be used on an industrial scale because di(chloromethyl)disilane is not an industrial product.

Thus, the industry is still seeking a safe and inexpensive method for the preparation of compounds of the hexaalkyldisilane type.

The present invention has enabled this object to be achieved and the subject thereof is a process for the preparation of hexaalkyldisilane, wherein:

(a) a trialkylsilane halide of formula (I)

(I)

wherein $R_1$, $R_2$ and $R_3$, which may be identical or different, represent an alkyl group containing 1 to 6 carbon atoms and X represents Cl, Br or I, is brought into contact with (b) an alkali metal selected from the group consisting of Na, Li and K and with (c) a salt $M^+ A^-$ wherein $A^-$ represents an anion selected from the group consisting of $Cl^-$, $Br^-$, $I^-$, $CN^-$, $SCN^-$, $RS^-$ $C_6H_4O^-$ and $RO^-$ in which R represents an alkyl radical containing 1 to 6 carbon atoms, $M^+$ represents a cation selected from the group consisting of an alkali metal cation, a $CH_3$ cation and a quaternary ammonium cation (d) in a solvent selected from the group consisting of aliphatic and aromatic hydrocarbons, and (e) in the presence of a phase transfer agent of the formula (II):

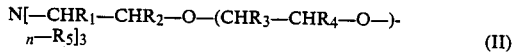

wherein n is an integer greater than or equal to 0 and less than or equal to approximately 10 ($0 \leq n \leq 10$), $R_1$, $R_2$, $R_3$ and $R_4$, which may be identical or different, represent a hydrogen atom or an alkyl radical containing 1 to 4 carbon atoms and $R_5$ represents an alkyl or cycloalkyl radical containing 1 to 12 carbon atoms, a phenyl radical or a radical of the formula $—C_mH_{2m}—\phi$ or $C_mH_{2m+1}—\phi—$, m ranging from 1 to about 12.

The use of trialkylsilane chlorides, especially trimethylchlorosilane chloride, is preferred because it is readily available.

The alkali metal identified above in (b) may be sodium, lithium or potassium. As stated earlier, the use of lithium and potassium is avoided in industrial applications because of the safety hazards involved in using them and their very high cost. The use of sodium is thus preferred.

The preferred salt of formula $M^+A^-$ identified above in (c) is a salt in which $M^+$ cation is that of an alkali metal identical to the alkali metal used in (b). The use of a sodium salt as $M^+A^-$ is thus preferred.

Among sodium salts, the use of a bromide or an iodide, particularly an iodide, which can be synthesized in situ by the reaction of iodine on sodium metal, is preferred.

The solvent identified above in (d) is selected from the group consisting of aliphatic and aromatic hydrocarbons. Toluene, xylene, decane, dodecane and decalin are illustrative solvents. The use of decalin is preferred.

As mentioned above, the phase transfer agents identified above in (e) are selected from those of the general formula (II):

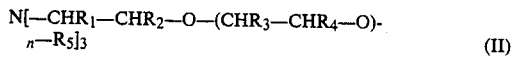

wherein n is an integer greater than or equal to 0 and less than or equal to approximately 10 ($0 \leq N \leq 10$), $R_1$, $R_2$, $R_3$ and $R_4$, which may be identical or different, represent a hydrogen atom or an alkyl radical containing 1 to 4 carbon atoms and $R_5$ represents an alkyl or cycloalkyl radical containing 1 to 12 carbon atoms, a phenyl radical or a radical of formula $—C_mH_{2m}—\phi—$ or $C_mH_{2m}—\phi—$, m ranging from 1 to about 12. In preferred phase transfer agents $R_1$, $R_2$, $R_3$ and $R_4$ represent a hydrogen atom or a methyl radical, n is greater than or equal to 0 and less than or equal to 6, and $R_5$ represents an alkyl radical containing not more than 4 carbon atoms.

Preferred compounds of formula (II) include:
tris(3-oxabutyl)amine of the formula:

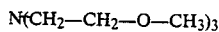

tris(3-oxaheptyl)amine of the formula:

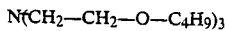

tris(3,6-dioxaheptyl)amine of the formula:

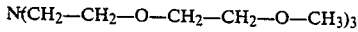

tris(3,6,9-trioxadecyl)amine of the formula:

N(CH$_2$—CH$_2$—O—CH$_2$—CH$_2$—O—CH$_2$—CH$_2$—O—CH$_3$)$_3$ tris(3,6-dioxaoctyl)amine of the formula:

N(CH$_2$—CH$_2$—O—CH$_2$—CH$_2$—OC$_2$H$_5$)$_3$ tris(3,6,9-trioxaundecyl)amine of the formula:

N(CH$_2$—CH$_2$—O—CH$_2$—CH$_2$—O—CH$_2$—CH$_2$—O—C$_2$H$_5$)$_3$ tris(3,6-dioxanonyl)amine of the formula:

N(CH$_2$—CH$_2$—O—CH$_2$—CH$_2$—O—C$_3$H$_7$)$_3$ tris(3,6,9-trioxadodecyl)amine of the formula:

N(CH$_2$—CH$_2$—O—CH$_2$—CH$_2$—O—CH$_2$—CH$_2$—O—C$_3$H$_7$)$_3$ tris(3,6-dioxadecyl)amine of the formula:

N(CH$_2$—CH$_2$—O—CH$_2$—CH$_2$—O—C$_4$H$_9$)$_3$ tris(3,6,9-trioxatridecyl)amine of the formula:

N(CH$_2$—CH$_2$—O—CH$_2$—CH$_2$—O—CH$_2$—CH$_2$—O—C$_4$H$_9$)$_3$ tris(2,6,9,12-tetraoxatridecyl)amine of the formula:

N(CH$_2$—CH$_2$—O(CH$_2$—CH$_2$—O—)$_3$—CH$_3$)$_3$ tris(3,6-dioxa-4-methylheptyl)amine of the formula:

N(CH$_2$—CH$_2$—O—CHCH$_3$—CH$_2$—O—CH$_3$)$_3$ and tris(3,6-dioxa-2,4-dimethylheptyl)amine of the formula:

N(CH$_2$—CHCH$_3$—O—CHCH$_3$—CH$_2$—O—CH$_3$)$_3$

The use of tris(3,6-dioxaheptyl)amine is very particularly preferred.

It is preferable to use a quantity of the salt M$^+$A$^-$ such that the molar ratio of the salt to alkylsilane halide ranges from 0.001:1 to 0.1:1, more preferably from 0.001:1 to 0.05:1, and most preferably from 0.005:1 to 0.02:1 and a quantity of phase transfer agent such that the molar ratio of the phase transfer agent to alkylsilane is from 0.01:1 to 0.10:1, more preferably from 0.02:1 to 0.10:1, and most preferably, approximately 0.05:1. It is preferred that the metal be used in an approximately molar, i.e., 1:1, quantity relative to the alkylsilane.

The reaction temperature must be above the melting point of the alkali metal. It preferably ranges from 100° to 180° C.

The reaction is conducted for a time sufficient to achieve the desired hexaalkyldisilane. As seen in the Examples, illustrative reaction times range from 4 to 16 hours.

The invention will be described more completely using the following examples which must not be regarded as limiting the invention.

EXAMPLES

Example 1

A 125 ml reactor was charged with 30 cm$^3$ of decalin and 5 g of sodium. The contents were heated to 130° C. with stirring, and 4 g of a 4 moles:1 mole mixture of tris(3,6-dioxaheptyl)amine:LiBr were then introduced. 23.5 g of trimethylchlorosilane were then added in the course of 2 hours. After 8 hours of reaction, hexamethyldisilane was obtained, with a yield of 75% relative to the trimethylchlorosilane product charged and a yield of 80% relative to the trimethylchlorosilane product actually converted, i.e., 5% of the trimethylchlorosilane starting material was not reacted.

Example 2

The procedure was the same as in Example 1, but 3.5 g of a 9 moles:1 mole mixture of tris(3,6-dioxaheptyl)amine:NaI were introduced. After 6 hours of reaction, hexamethyldisilane was obtained, with a yield of 90% relative to the trimethylchlorosilane product charged and a yield of 93% relative to the trimethylchlorosilane product actually converted. In this Example, 3% of the trimethylchlorosilane starting material was not reacted.

Example 3

The procedure was identical to that in Example 1, but 4.3 g of a 95 moles:5 moles mixture of tris(3,6-dioxaheptyl)amine:I$_2$ were introduced. After 6 hours of reaction, hexamethyldisilane was obtained, with a yield of 87% relative to the trimethylchlorosilane product charged and a yield of 89% relative to the trimethylchlorosilane product actually converted.

Example 4

The procedure was the same as in Example 1, but 3.5 g of a 9 moles:1 mole mixture of tris(3,6-dioxaheptyl)amine:NaI were introduced. 33 g of butyldimethylchlorosilane were then introduced in the course of 2 hours. After 8 hours of reaction, tetramethyldibutyldisilane was obtained with a yield of 85% relative to both the butyldimethylchlorosilane product charged and the butylmethylchlorosilane product converted.

Examples 5 to 8

0.21 mole of trimethylchlorosilane were injected into a mixture of 0.21 gram-atom of sodium, the phase transfer agent tris(dioxaheptyl)amine and lithium bromide in 60 ml of decalin. The mole percents of the phase transfer agent and lithium bromide relative to the trimethylchlorosilane in each Example are recited below, as also are the times of reaction and the yields obtained. Note that Example 7, which uses no phase transfer agent, was a comparative example.

| Example | Tris(dioxaheptyl)amine mol % | LiBr mol % | Period | Yield/ (CH$_3$)$_3$SiCl converted | Total yield |
| --- | --- | --- | --- | --- | --- |
| 5 | 9.2 | 9.2 | 6 | 63 | 61 |
| 6 | 4.8 | 4.8 | 6 | 57 | 44 |
| 7 | 0 | 6.1 | 5 h 30 | 0 | 0 |
| 8 | 2.4 | 2.4 | 7 | 66 | 46 |

Examples 9 to 19

These examples are used to illustrate the nature of the salt M$^+$A$^-$ employed. Note that Example 9 used no salt and was thus a comparative example.

| Example | Period | Na* | Amine* | Salt* | Me₃SiCl* | Nature of the salt | Final yield |
|---|---|---|---|---|---|---|---|
| 9 | 8 h 30 | 7 | 0.35 | 0 | 7 | none | 32 |
| 10 | 6 h 10 | 7 | 0.35 | 0.08 | 7 | LiCl | 72 |
| 11 | 8 h 30 | 7 | 0.35 | 0.08 | 7 | LiBr | 74 |
| 12 | 8 h | 7 | 0.35 | 0.08 | 7 | LiI | 76 |
| 13 | 4 h | 7 | 0.35 | 0.08 | 7 | NaI | 72 |
| 14 | 5 h | 7 | 0.35 | 0.04 | 7 | NaI | 89 |
| 15 | 15 h | 7 | 0.35 | 0.04 | 7 | KI | 74 |
| 16 | 8 h | 7 | 0.35 | 0.04 | 7 | N(Bu)₄I | 81 |
| 17 | 10 h | 7 | 0.35 | 0.04 | 7 | CH₃I | 62 |
| 18 | 6 h | 7 | 0.35 | 0.04 | 7 | I₂ | 86 |
| 19 | 15 h | 7 | 0.35 | 0.04 | 7 | KI | 74 |

*moles of the reagent per liter of decalin

Examples 20 to 25

These examples illustrate the effect of variations in the concentration of the salt and in the amine used as the phase transfer agent.

| Example | NaI* | Me₃SiCl* | Na* | amine* | Period | Yield |
|---|---|---|---|---|---|---|
| 20 | 0.08 | 7 | 7 | 0.35 | 4 h | 72 |
| 21 | 0.04 | 7 | 7 | 0.35 | 8 h | 79 |
| 22 | 0.02 | 7 | 7 | 0.35 | 16 h | 76 |
| 23 | 0.02 | 7 | 7 | 0.37 | 6 h | 87 |
| 24 | 0.04 | 7 | 7 | 0.17 | 5 h 30 | 90 |
| 25 | 0.10 | 7 | 7 | 0.10 | 5 h 30 | 87 |

*moles of the reagent per liter of decalin

What is claimed is:

1. A process for the preparation of hexaalkyldisilane comprising the step of contacting
   (a) a trialkylsilane halide of the formula (I)

　　　(I)

wherein $R_1$, $R_2$ and $R_3$, which may be identical or different, represent an alkyl group containing 1 to 6 carbon atoms and X represents Cl, Br or I, with
   (b) an alkali metal selected from the group consisting of Na, Li and K and with
   (c) a salt $M^+A^-$,
wherein $A^-$ represents an anion selected from the group consisting of $Cl^-$, $Br^-$, $I^-$, $CN^-$, $SCN^-$, $RS^-$, $C_6H_4O^-$ and $RO^-$, wherein R represents an alkyl group containing 1 to 6 carbon atoms, and
   $M^+$ represents a cation selected from the group consisting of an alkali metal cation, a $CH_3$ cation, and a quaternary ammonium cation,
   (d) in a solvent selected from the group consisting of aliphatic and aromatic hydrocarbons, and
   (e) in the presence of a phase transfer agent of the formula (II):

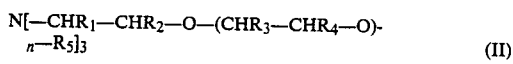　　　(II)

wherein n is an integer greater than or equal to 0 and less than or equal to approximately 10 ($0 \leq n \leq 10$), $R_1$, $R_2$, $R_3$ and $R_4$, which may be identical or different, represent a hydrogen atom or an alkyl radical containing 1 to 4 carbon atoms and $R_5$ represents an alkyl or cycloalkyl radical containing 1 to 12 carbon atoms, a phenyl radical or a radical of the formula $-C_mH_{2m}-\phi-$ or $C_mH_{2m+1}-\phi-$, m ranging from 1 to approximately 12.

2. The process of claim 1, wherein the trialkylsilane halide is a trialkylsilane chloride.

3. The process of claim 1, wherein the alkali metal is Na.

4. The process of claim 1, wherein $A^-$ is an iodide or a bromide.

5. The process of claim 4, wherein $A^-$ is an iodide.

6. The process of claim 1, wherein $M^+$ is $Na^+$.

7. The process of claim 1, wherein the alkali metal is Na and the $M^+A^-$ salt is sodium iodide.

8. The process of claim 1, wherein the molar ratio of the salt $M^+A^-$ to the trialkylsilane halide ranges from 0.001:1 and 0.1:1.

9. The process of claim 8, wherein said molar ratio ranges from 0.001:1 to 0.05:1.

10. The process of claim 9, wherein said molar ratio ranges from 0.005:1 to 0.02:1.

11. The process of claim 1, wherein the molar ratio of the phase transfer agent of formula (II) to the trialkylsilane ranges from 0.01:1 to 0.10:1.

12. The process of claim 11, wherein said molar ratio ranges from 0.02:1 to 0.10:1.

13. The process of claim 12, wherein said molar ratio is approximately 0.05:1.

* * * * *